United States Patent
Burgath et al.

(10) Patent No.: US 6,670,436 B2
(45) Date of Patent: Dec. 30, 2003

(54) THERMOCHROMIC DENTAL MATERIAL

(75) Inventors: Armin Burgath, Bodman-Ludwigshafen (DE); Peter Burtscher, Nütziders (AT); Ulrich Salz, Lindau (DE); Volker Rheinberger, Vaduz (LI)

(73) Assignee: Ivoclar Vivadent AG (LI)

( * ) Notice: Subject to any disclaimer, the term of this patent is extended or adjusted under 35 U.S.C. 154(b) by 75 days.

(21) Appl. No.: 10/068,581

(22) Filed: Feb. 6, 2002

(65) Prior Publication Data

US 2002/0152929 A1 Oct. 24, 2002

(30) Foreign Application Priority Data

Feb. 12, 2001 (DE) .......................................... 101 06 372

(51) Int. Cl.[7] .................................................. C08F 2/00
(52) U.S. Cl. ........................ 526/213; 526/204; 526/208; 526/217; 526/321; 526/323.1; 526/323.2; 526/328.5
(58) Field of Search ................................. 526/204, 208, 526/213, 217, 321, 323.1, 323.2, 328.5

(56) References Cited

U.S. PATENT DOCUMENTS

| 3,600,060 A | 8/1971 | Churchill et al. |
| 3,619,254 A | 11/1971 | Davis |
| 4,022,706 A | 5/1977 | Davis |
| 4,600,389 A | 7/1986 | Schwartz |
| 4,957,949 A | 9/1990 | Kamada et al. |
| 5,102,461 A | 4/1992 | Rheinberger et al. |
| 5,162,130 A | 11/1992 | McLaughlin |
| 5,431,697 A | 7/1995 | Kamata et al. |
| 5,655,592 A | 8/1997 | Sullivan |
| 5,698,020 A | 12/1997 | Salz et al. |
| 6,491,037 B1 * | 12/2002 | Mortenson .................. 128/859 |

FOREIGN PATENT DOCUMENTS

| DE | 690 19 991 T2 | 6/1990 |
| DE | 195 02 751 A1 | 1/1995 |
| DE | 195 25 941 A1 | 7/1995 |
| EP | 0 389 239 A1 | 9/1990 |
| EP | 0 610 072 A1 | 8/1994 |
| WO | WO 92/00056 | 1/1992 |

* cited by examiner

Primary Examiner—Helen L. Pezzuto
(74) Attorney, Agent, or Firm—Nixon Peabody LLP

(57) ABSTRACT

The invention relates to dental materials which contain a thermochromic dye and which display a reversible change of colour in the event of changes in temperature, so that they can be distinguished from the natural dentin.

15 Claims, No Drawings

THERMOCHROMIC DENTAL MATERIAL

The invention relates to dental materials which contain a thermochromic dye and which display a reversible change of colour in the event of temperature changes.

For aesthetic reasons, tooth-coloured restoration materials are increasingly being used in restorative dentistry. These materials have the disadvantage that they can be visually distinguished from the natural tooth substance only with difficulty, with the result that the removal of excess material and also the reworking and matching for example of fillings is made difficult. The consequence is that, frequently, healthy tooth substance is unnecessarily removed or on the other hand excess dental material is overlooked which can then, as a retention niche, encourage the formation of plaque and lead to parodontal problems. Also, when tooth-coloured fillings are removed, because of the poor visibility of the transition area between filling and tooth substance, it often happens that either too much healthy tooth substance is removed or else remains of the filling are overlooked. Similar problems result when using tooth-coloured fixing materials for the cementing of tooth-coloured restorations.

EP 0 610 072 A2 relates to toothbrushes which contain a thermochromic material and which, during use, show the cleaning time by changing colour.

U.S. Pat. No. 4,957,949 discloses masterbatches which contain wax and a granular thermochromic material homogeneously dispersed therein, which is coated with a high-molecular-weight, hydrophilic substance. The masterbatches are said to be able to be incorporated into thermoplastics even at high temperatures and pressures without loss of the thermochromic properties. The dye-containing thermoplastics are said to be particularly suitable for the manufacture of toothbrushes.

U.S. Pat. No. 5,431,697 discloses compositions on the basis of olefin polymers which contain thermochromic dyes. The dyes are preferably used in a granular form which can be obtained by mixing polymer and dye and then crosslinking the polymer. The obtained granular material is said to be suitable in particular for mixing with thermoplastics, which can then be further processed to give toothbrushes which change colour.

U.S. Pat. No. 3,619,254 discloses multi-layered articles which, in addition to a base layer and at least one protective layer, include a thermochromic layer which contains liquid-crystalline, thermochromic dyes. The articles are said to be suitable in the form of rectangular strips for the measurement of body temperature.

U.S. Pat. No. 4,022,706 discloses thermochromic, liquid-crystalline printing dyes in the form of viscous oil-in-water emulsions which are said to be suitable in particular for the imprinting of films and laminates. The printing dyes are deposited onto the films and not incorporated in them.

Dental materials are disclosed in U.S. Pat. No. 5,162,130, the colouring of which can be set by irradiation with UV light followed by heating. The materials undergo a permanent change of colour and are not suitable for the temporary visualization of colourless or tooth-coloured dental materials.

DE 195 02 751 A1 discloses a process for the manufacture of plastic models for dental engineering, which are characterized by a high-contrast, coloured surface. This is achieved by integration for example of a thermochromic dye into the surface of the model.

Dental materials which contain a thermochromic dye are not known at present.

The object of the present invention is to create a dental material, the colour of which can be temporarily changed in a simple way such that the material can be visually distinguished from the natural tooth substance, and which again assumes its original colour after a period sufficient for the working of the dental material.

This object is achieved by dental materials which, in addition to at least one polymerizable ethylenically unsaturated monomer and at least one initiator for cold, hot and/or photopolymerization, contain at least one thermochromic dye.

By dental materials is meant materials which are suitable for use in the patient's mouth, i.e. for example as a dental restoration, as a constituent of a dental restoration or serve to fix a dental restoration or orthopaedic device in the patient's mouth.

By thermochromic dyes are meant inorganic or preferably organic substances which reversibly change their colour according to the temperature.

According to the invention, thermochromic dyes are preferred which are colourless at a temperature of approx. 37° C. and which change colour upon heating or preferably cooling, i.e. assume a colour that can clearly be distinguished from the natural tooth substance. At a temperature of approx. 37° C. the colour of the dental material is thus determined by its intrinsic colour.

Particularly preferred are thermochromic dyes which change colour at a temperature of 29° C. or less, preferably of 5 to 29° C., in particular 12 to 29° C. and quite particularly preferably 20 to 29° C., or materials which change colour at temperatures of 40° C. or more, preferably 40 to 60° C. and in particular 45 to 55° C.

Furthermore, dyes are preferred which assume a red, blue or black colouring and can thus be distinguished particularly well from the natural tooth substance.

Thermochromic dyes are preferred which contain an electron donor and an electron acceptor, or dyes which contain an acid-responsive component and an acidic component, Mixtures of an electron-emitting chromogen (electron donor) and an electron acceptor are particularly suitable as thermochromatic dyes on the basis of an electron donor and electron acceptor. Preferred as electron donors are substituted phenyl-methanes, fluoranes, such as for example 3,3'-dimethoxy-fluorane, 3-chloro-6-phenylamino-flourane, 3-diethylamino-6-methyl-7-chlorofluorane, 3-diethyl-7,8-benzofluorane, 3,3', 3"-tris(p-di-methylaminophenyl) phthalide, 3,3'-bis(p-dimethyl-aminophenyl)-7-phenylaminofluorane and 3-diethyl-amino-6-methyl-7-phenylamino-fluorane, indolylphthalides, spiropy-ranes and cumarins, as well as mixtures of these substances.

Particularly suitable as electron acceptors are phenols, azoles, organic acids and esters as well as salts of organic acids. Examples that may be cited as phenols are phenylphenol, bisphenol A, cresol, resorcinol, chlorolucinol, phenol, phenol oligomers, β-naphthol, 1,5-dihydroxynaphthalene, pyrocatechol, pyrogallol, and the trimer of p-chlorophenol formaldehyde condensate. Examples that may be cited as azoles are benzo-triazoles, such as 5-chlorobenzo-triazole, 4-laurylaminosulfo-benzotriazole, 5-butylbenzotriazole, dibenzotrizaole, 2-oxy-benzotriazole, 5-ethoxy-carbonylbenzo-triazole, 5,5'-methylene-bisbenzotriazole, imidazole, such as oxybenzimidazole, and tetrazole. The organic acids comprise for example aromatic and aliphatic carboxylic acids and substituted derivatives thereof. Examples of aromatic carboxylic acids are salicylic acid, methylenebissalicylic acid, β-resorcylic acid, gallic acid, benzoic acid, p-oxybenzoic acid, pyromellitic acid, β-naphthoic acid, tannic acid, toluic acid, trimellitic acid, phthalic acid, terephthalic acid and anthranalic acid. Examples of aliphatic carboxylic acids are acids with 1 to 20 carbon atoms, preferably 3 to 15 carbon atoms, such as for example stearic acid, 1,2-hydroxystearic acid, tartaric acid, citric acid, oxalic acid and lauric acid. Examples of esters are alkyl esters of aromatic carboxylic acids in which the alkyl group contains 1 to 6 carbon atoms, such as butyl gallate, ethyl-p-hydroxybenzoate and methyl salicylate. Examples that may be cited as salts are ammonium and metal salts of the above-named acids. The metal salts comprise for example lithium, sodium, calcium, magnesium, aluminium, zinc, tin, titanium and nickel salts. Particularly preferred electron acceptors are 1,2-hydroxystearic acid, tartaric acid and citric acid. The above-named electron acceptors can be used alone or mixed with one another. Furthermore, the thermochromic materials can be used as such or in microencapsulated form. Suitable dyes of this type are described in U.S. Pat. No. 4,957,949.

Preferred as thermochromic dyes on the basis of an acid-responsive component and an acidic component are mixtures of an acid-responsive chromogenic substance and an acidic substance (acid component).

Preferred acid-responsive substances are triphenyl-methane phthalides, phthalides, phthalanes, acyl-leucomethylene blue compounds, fluoranes, triphenylmethanes, diphenylmethanes, spiropyranes and derivatives of these substances. Examplary compounds are 3,6-dimethoxyfluorane, 3,6-di-butoxyfluorane, 3-diethylamino-6,-dimethylfluorane, 3-chloro-6-phenylamino-fluorane, 3-diethylamino-6-methyl-7-chloro-fluorane, 3-diethyl-amino-7,8-benzofluorane, 2-anilino-3-methyl-6-diethylamino-fluorane, 3,3', 3"-tris(p-dimethylamino-phenyl)phthalide, 3,3'-bis(p-dimethyl-aminophenyl)phthalide, 3-diethylamino-7-phenyl-aminofluorane, 3,3-bis(p-diethylamino-phenyl)-6-dimethylamino-phthalide, 3-(4-diethylaminophenyl)-3-(1-ethyl-2-methylindol-3-yl)phthalide,3-(4-diethylamino-2-methyl)phenyl-3-(1,2-dimethylindol-3-yl)phthalide and 2'-(2-chloranilino)-6'-dibutylamino-spiro-[phthalido-3,9'-xanthene].

Preferred acidic substances are 1,2,3-benzotriazoles, phenols, thioureas, oxoaromatic carboxylic acids and derivatives of these substances. Examplary compounds are 5-butylbenzotriazole, bisbenzotrizaol-5-methane, phenol, nonylphenol, bisphenol A, bisphenol F, 2,2'-biphenol, β-naphthol, 1,5-dihydroxynaphthalene, alkyl-p-hydroxybenzoates and phenolic resin oligomers. These dyes can likewise be used as such or in micro-encapsulated form. Suitable dyes of this type are described in U.S. Pat. No. 5,431,697 and can be obtained from the companies Dain-ichiseika Color & Chemicals Co., Ltd, for example under the name Yellow PP-020®, from Hodogaya Chemical Co., Ltd., or from Matsui Shikiso Chemical Co., Ltd., for example under the names Photopia Yellow® or Chromicolor Fast Blue S-17®.

Further preferred thermochromic dyes are liquid crystalline cholesterol derivatives, such as alkanic acid and aralkanic acid esters of cholesterol, alkyl esters of cholesterol carbonate and mixtures thereof, in particular those with alkyl and alkanic acid groups with 1 to 24 carbon atoms. Cholesterol esters and derivatives thereof which contain an alkanic acid group with 9 to 22 carbon atoms or an aralkanic acid group with a benzoic acid group and 1 to 3 carbon atoms in the alkyl part are particularly preferred. In the case of the cholesterol carbonate esters, those with $C_1$ to $C_{20}$ alkyl groups are preferred. Suitable compounds of this type are described in U.S. Pat. No. 3,619,254.

Further preferred liquid-crystalline cholesterol derivatives are cholesterol chloride, cholesterol bromide, cholesterol acetate, cholesterol oleate, cholesterol caprylate, cholesterol oleyl-carbonate, mixtures thereof and mixtures of these dyes with the previously named cholesterol derivatives. These and other dyes are described in U.S. Pat. Nos. 4,022,706 and 3,600,060. Suitable dyes can be obtained from the company Davis Liquid Crystals, Inc., USA under the name Chromazone®.

Thermochromic dyes are preferably used in a quantity of 0.01 to 2 wt.-%, particularly preferably 0.1 to 0.5 wt.-% and quite particularly preferably in a quantity of approx. 0.2 wt.-% relative to the total mass of the dental material.

The dental materials according to the invention are colourless, i.e. not coloured, at body temperature, i.e. at approx. 37° C., and can have their colour changed by heating or preferably by cooling. This can take place for example by rinsing the patient with a cold or warm liquid before or during a treatment by the dentist or by having the dentist cool the tooth in question with an air-jet. The coloured dental material can then be well distinguished from the natural tooth substance and can thus be worked by the dentist in a targeted way.

In addition to the thermochromic material, the dental materials according to the invention contain at least one ethylenically unsaturated monomer as binder and at least one initiator for hot, cold or preferably photopolymerization. In addition, the dental materials preferably also contain organic and/or inorganic filler.

Suitable as polymerizable organic binders are all binders that can be used for a dental material, in particular mono-functional or polyfunctional methacrylates which can be used alone or in mixtures. Examplary binders are methyl methacrylate, isobutyl methacrylate, cyclohexyl methacrylate, tetraethylene glycol dimethacrylate, triethylene glycol dimethacrylate, diethylene glycol dimethacrylate, ethylene glycol dimethacrylate, polyethylene glycol dimethacrylate, butanediol dimethacrylate, hexanediol dimethacrylate, decanediol dimethacrylate, dodecanediol dimethacrylate, bis-phenol-A-dimethacrylate, trimethylolpropane trimethacrylate, 2,2-bis-[4-(2-hydroxy-3-methacryloxypropoxy)-phenyl]-propane(bis-GMA), as well as the reaction products of iscocyanates, in particular di- and/or triisocyanates and OH-group-containing methacrylates. Examples of these are the reaction products of 1 mol hexamethylene diisocyanate with 2 mol 2-hydroxyethylene methacrylate, of 1 mol tri-(6-isocyanatohexyl)bluret with 3 mol 2-hydroxyethyl methacrylate and of 1 mol 2,2,4-trimethyl-hexamethylene diisocyanate with 2 mol 2-hydroxyethyl methacrylate, which are called urethane dimethacrylates in the following. The proportion of these mostly long-chained compounds in the dental material varies between 10 and 80 wt.-%.

Particularly preferred are 2,2-bis-[4-(2-hydroxy-3-methacryloxy-propoxy)-phenyl]-propane (bisphenol-A-diglycidyldimeth-acrylate, bis-GMA), 7,7,9-trimethyl-4,13-dioxo-3,14-dioxa-5,12-diazahexa-decan-1,16-dioxydimethacrylate, triethylene glycol dimethacrylate, 1,10-decanediol dimethacrylate and mixtures of these monomers.

Preferred as initiators for the hot-curing systems are peroxides, in particular t-butyl peroxide, dibenzoyl peroxide, dilauroyl peroxide, tert.-butyl peroctoate and tert.-butyl perbenzoate. Moreover, 2,2'-azoisobutyronitrile (AIBN), benzopinacol and 2,2'-dialkybenzopinacols are also suitable. Hot-curing dental materials are particularly suitable for the production of inlays and onlays.

Used as initiators for cold polymerization are radical-supplying systems, for example benzoyl peroxide, lauroyl peroxide or preferably dibenzoyl peroxide, together with amines such as N,N-dimethyl-p-toluidine, N,N-dihydroxyethyl-p-toluidine or other structurally related amines.

Amine and peroxide are usually distributed over two different components of the dental material. Upon mixing of the amine-containing base paste with the peroxide-containing initiator paste, radical polymerization is initiated by the reaction of amine and peroxide.

There can be used, as initiators for photopolymerization, benzo-phenone and its derivatives for example, as well as benzoin and its derivatives. Further preferred photoinitiators are the α-diketones such as 9,10-phenanthrenequinone, diacetyl, furil, anisil, 4,4'-dichlorobenzil, 4,4'-dialkoxybenzil, phenylpropanedione and acylphosphine oxides. Camphorquinone is particularly preferably used. Photopolymerization is preferably initiated by irradiation with light in a wavelength range from 400 to 500 nm.

Combinations of cold and photoinitiators are suitable as initiators for dual-curable systems. By way of example, the base paste can additionally contain a photoinitiator, so that the base paste can be used either alone as a light-curing dental material, or together with the initiator paste as a light- and self-curing dental material. The use of camphor-quinone and dibenzoyl peroxide in combination with the above-named amines is preferred.

Dental materials which contain an initiator for cold polymerization and in particular for photopolymerization are preferred.

Suitable as filler components are, in particular, amorphous spherical materials on the basis of mixed oxides of $SiO_2$, $ZrO_2$ and/or $TiO_2$ with an average particle size of 0.005 to 2.0 μm, preferably 0.1 to 1 μm, such as are disclosed for example in DE-PS 32 47 800, microfine fillers, such as pyrogenic silica or precipitated silica as well as macro- or mini-fillers, such as quartz, glass ceramic or glass powder, barium silicate glasses, barium fluorosilicate glasses and Li/Al silicate glasses, barium glasses, the oxides of aluminium or silicon, with an average particle size of 0.01 to 20 μm, preferably 0.5 to 5 μm, as well as X-ray-opaque fillers. By mini-fillers are meant fillers with a particle size of 0.5 to 1.5 μm and, by macro-fillers, fillers with a particle size of 10 to 20 μm.

Suitable X-ray-opaque fillers, the average particle size of which should not exceed 5.0 μm, are described in DE-OS 35 02 594. Ytterbium trifluoride is particularly preferred.

Preferably used as filler is a mixture of (A) amorphous, spherical particles of silicon dioxide and up to 20 mol-% of an oxide of at least one element of groups I, II, III and IV of the periodic system with a refractive index of 1.50 to 1.58 and with an average primary particle size of 0.1 to 1.0 μm, and (B) quartz, glass ceramic or glass powder or their mixtures with a refractive index of 1.50 to 1.58 and with an average particle size of 0.5 to 5.0 μm.

The inorganic filler (A) preferably contains strontium and/or zirconium oxide as oxide of a metal of groups I, II, III and IV of the periodic system. The average primary particle size lies preferably in the range from 0.15 to 0.5 μm, and the refractive index of the inorganic filler (A) preferably between 1.52 and 1.56. A particularly preferred value is 1.53±0.01. Fillers of type (A) are described in DE-PS 32 47 800. The filler of type (A) can also be present sintered as a mixture of agglomerates with an average particle size of 1 to 30 μm.

The average primary particle size of the inorganic filler (B) lies preferably between 1.0 and 2.0 μm and particularly preferably between 1.0 and 1.5 μm, while the refractive index is to display values preferably between 1.52 and 1.56. Filler mixtures can also be used. Preferred according to the invention are Ba-silicate glasses with an average grain size in the range from 1.1 to 1.3 μm, as well as Sr-silicate glasses with an average grain size in the range from 1.1 to 1.3 μm, and also Li/Al silicate glasses with an average grain size from 1.0 to 1.6 μm. Such powders can be obtained e.g. by fine grinding with a RS ultrafine mill from the company Reimbold & Strich, Cologne.

Optionally, the mixture of fillers (A) and (B) can also contain further fillers (C) in order to achieve an increased X-ray capacity and/or fillers (D) in order to set the viscosity. Microfine, pyrogenic or wet-precipitated silica is preferred as filler (D). The quantity of filler (D) is at most 5 wt.-%, relative to the dental material.

Further preferred fillers are described in DE 40 29 230.

The inorganic fillers are preferably silanized. In particular, α- and γ-methacryloxypropyltrimethoxysilane and similar substances known per se are preferred as adhesion promoters.

Furthermore, fine-particled splitter or bead polymerizates, which can be homo- or copolymers of the already described monomers, can be incorporated in the dental material. These homo- or copolymers can for their part be filled with the described inorganic fillers, including X-ray opaque. Moreover, the dental material can contain the usual pigmentation agents and stabilizers.

The thermochromic dyes preferred according to the invention are compatible with the most varied dental materials and prove to be advantageous particularly upon incorporation into colourless or tooth-coloured dental materials, as they essentially do not lead to a visible change in the colour of the material. The dental materials are characterized by a permanent reversibility of the change of colour, which is not adversely affected by the curing of the materials. In addition, the change of colour can be induced without the risk of premature curing.

Dental materials within the meaning of the invention are in particular sealers, permanent and temporary filling materials, cements for inlays, onlays, crowns and bridges, in particular cements for orthodontics (KFO cements), i.e. cements for the fixing of brackets and tooth braces, varnishes, such as for example fluoride varnishes, stump construction materials, plaque indicators and adhesives. Adhesives are, generally, un-filled, whereas cements, generally, contain filler. Adhesives act as bond promoters between dentin and restoration and can be used in combination with a cement. Anhydrous dential materials and in particular solvent-free dental materials are preferred.

Due to the presence of the thermochromic dye, the dentist can ensure a deposition over the full surface in the case of sealers, adhesives and varnishes, and render material residues visible in the case of filling materials and cements and distinguish with certainty between dental material and natural tooth substance.

The dental materials according to the invention preferably contain more than 10 wt.-%, particularly preferably more than 20 wt.-% of polymerizable monomer. The filler content preferably lies in the range from 10 to 90 wt.-%. The dental materials are produced by working dye, polymerization initiator and optionally filler and additives into the binder until a homogeneous mixture of the constituents is obtained.

Materials of the following composition are quite particularly preferred:

(a) >10 to 99.98 wt.-%, preferably >20 to 90 wt.-% polymerizable monomer; and/or (b) 0.01 to 2 wt.-%, preferably 0.1 to 0.5 wt.-% thermochromatic dye; and/or (c) 0.01 to 5 wt.-%, preferably 0.1 to 3 wt.-% polymerization initiator; and/or (d) 0 to <89.98 wt.-%, preferably 10 to 80 wt.-% and quite particularly preferably 20 to 70 wt.-% filler; and/or (e) optionally 0.01 to 5 wt.-% further additives.

By additives is meant customary added substances, such as stabilizers, UV absorbers, polymerization inhibitors, dyes, pigments and lubricants.

The filler content is decisively determined by the desired use of the dental material. For use as an adhesive, filler-free materials are preferred, filling materials preferably contain from 60 to 85 wt.-% filler and cements preferably contain from 50 to 80 wt.-% filler.

The invention is explained in more detail in the following with reference to examples. The dyes used in the examples contain, as thermochromic dye, either an acid-responsive component and an acidic component or an electron donor and an electron acceptor. The quantities quoted in the examples are percentages by weight unless otherwise stated.

EXAMPLE 1

Light-Curing Filling Material

To produce a light-curing filling material, 0.2% (this and the following percentages relate, unless otherwise stated, to the total mass of the dental material) of Chromazone Red® (thermo-chromic dye; Davis Liquid Crystals; the colouring properties of the dyes are based on electron donor/electron acceptor inter-actions) were dispersed by means of a disperser in 21.1% of a monomer mixture of the composition given below. This mixture was then processed with 51.7% barium silicate glass powder, 5% barium fluorosilicate glass powder, 5% pyrogenic silica and 17% ytterbium trifluoride to produce a homogeneous composite. This was cured by three-minute irradiation with light of a wavelength of 400 to 500 nm. The cured material displayed a change of colour at 29° C., it was coloured red at temperatures below 29° C. and after the temperature was raised to above 29° C. the red colouring disappeared and the material again displayed its intrinsic colour. This procedure was able to be repeated as often as wished.

| Monomer mixture | |
|---|---|
| Bis-GMA | 42.1% |
| 7,7,9-trimethyl-4,13-dioxo-3,14-dioxa-5,12-diazahexadecan-1,16-dioxy-dimethacrylate (diurethane dimethacrylate) | 37% |
| Triethylene glycol dimethacrylate | 20% |
| Camphorquinone | 0.3% |
| Hydroquinone monoethyl ether | 0.1% |
| Ethyl-4-dimethylaminobenzoate | 0.5% |

The percentages relate to the mass of the monomer mixture.

EXAMPLE 2

Light-curing Filling Material

Example 1 was repeated, using the thermochromic dye Chromazone Blue® (Davis Liquid Crystals). The components were mixed with one another on a roll mill and the composite was cured as described in Example 1. The cured material displayed a reversible change of colour at 29° C., it was coloured blue at temperatures below 29° C. and at temperatures above 29° C. it was tooth-coloured.

EXAMPLE 3

Dual-curing Filling Material

To produce a dual-curing composite consisting of initiator and base pastes, 0.05% PSD-O (Orange pigment from Shin-Nisso Kako K.K.) was first dispersed in 26.45% monomer mixture of the composition given below. 43.5% silanized barium silicate glass powder, 5% barium fluorosilicate glass powder and 25% ytterbium trifluoride were then worked into this dispersion and a homogeneous paste was produced.

| Monomer mixture of the Base Paste | |
|---|---|
| Bis-GMA | 49.2% |
| 7,7,9-trimethyl-4,13-dioxo-3,14-dioxa-5,12-diazahexadecan-1,16-dioxy-dimethacrylate (diurethane dimethacrylate) | 24.8% |
| Triethylene glycol dimethacrylate | 24.7% |
| Camphorquinone | 0.3% |
| Ethyl-4-dimethylaminobenzoate | 0.4% |
| 2,6-di-tert.-butyl-p-cresol | 0.1% |
| N,N-3,5-di-tert.-butylaniline | 0.5% |

The percentages relate to the mass of the monomer mixture.

To produce the initiator paste, 0.05 PSD-O was dispersed in 28.75% monomer mixture of the composition given below. The dispersion was then processed with 46.2% silanized barium silicate glass powder and 25% ytterbium trifluoride to produce a homogeneous paste.

| | |
|---|---|
| Bisphenol-A-diglycidyldimethacrylate (bis-GMA) | 50.0% |
| 7,7,9-trimethyl-4,13-dioxo-3,14-dioxa-5,12-diazahexadecan-1,16-dioxy-dimethacrylate (diurethane dimethacrylate) | 24.2% |
| Triethylene glycol dimethacrylate | 24.2% |
| Benzoyl peroxide | 1.5% |
| 2,6-di-tert.-butyl-p-cresol | 0.1% |

The percentages relate to the mass of the monomer mixture.

After the mixing of equal proportions of base paste and initiator paste the mixture cured completely within three minutes at room temperature. The cured material displayed a reversible change of colour at 30° C., it was coloured orange below this temperature and at higher temperatures it displayed its whitish intrinsic colour.

EXAMPLE 4

Dental Sealing Material

To produce a sealing material, 0.8% microencapsulated thermochromic dye Chromicolor® Fast Blue S-17 (mixture of an acid-responsive chromogenic substance and a phenolic acid; manufacturer Matsui Shikiso Chemical Co.) was dispersed by means of a disperser in a mixture of 59.2% bisphenol-A-diglycidyl dimethacrylate (bis-GMA), 39.2% triethylene glycol dimethacrylate, 0.3% camphorquinone, 0.1% hydroquinone mono-ethyl ether and 0.4% ethyl-(4-dimethylamino)-benzoate. Curing took place by illumination with blue light in a wavelength range from 400 to 500 nm for 3 minutes. The material displays a reversible change of colour at 25° C., below this temperature it is coloured blue, above it it is practically colourless. The material is particularly suitable for use as a crack sealer.

EXAMPLE 5

Dental KFO Cement

To prepare a KFO cement, 1.0% of the microencapsulated thermochromic dye Chromicolor Yellow S-17 (thermochromic acid-responsive component with a phenolic acid component; manufacturer Matsui Shikiso Chemical Co.) was worked on a roll mill into 87.8% of the monomer mixture described in more detail below. The mixture was then reacted with 11.2% silanized barium glass powder.

| Monomer mixture | |
| --- | --- |
| Bis-GMA | 64.9% |
| 7,7,9-trimethyl-4,13-dioxo-3,14-dioxa-5,12-diazahexadecan-1,16-dioxy-dimethacrylate (diurethane dimethacrylate) | 19.8% |
| 1,10-decanediol dimethacrylate | 14.9% |
| Camphorquinone | 0.3% |
| 2,6-di-tert.-butyl-p-cresol | 0.1 |

The percentages relate to the mass of the monomer mixture.

Curing of the cement took place by means of blue light at 470 nm by illumination for 40 seconds. The cement is deposited onto the tooth for the fixing of brackets and cured by illumination by means of blue light in the wavelength range from 400 to 500 nm for 40 seconds. The material displays a reversible change of colour at 20° C., below this temperature it is coloured yellow, above it it displays its intrinsic colour.

What is claimed is:

1. Dental material comprising at least one polymerizable ethylenically unsaturated monomer, at least one initiator for cold, hot and/or photopolymerization, and at least one thermochromic dye.

2. Dental material according to claim 1, wherein said monomer comprises at least one of a monofunctional and poly-functional methacrylate.

3. Dental material according to claim 1, wherein said dental material contains more than 10 wt. % monomer.

4. Dental material according to claim 1, wherein said dental material contains from 0.01 to 2 wt. % thermochromic dye.

5. Dental material according to claim 1, wherein said thermochromic dye is colorless at body temperature and undergoes a reversible change of color upon cooling.

6. Dental material according to claim 5, wherein said thermochromic dye changes color at a temperature of 29° C. or less.

7. Dental material according to claim 6, wherein said thermochromic dye changes color at a temperature of from 40 to 60° C.

8. Dental material according to claim 1, wherein said thermochromic dye contains an electron donor and an electron acceptor.

9. Dental material according to claim 1, wherein said thermochromic dye contains an acid-responsive component and an acidic component.

10. Dental material according to claim 1, wherein said thermochromic dye contains a liquid-crystalline cholesterol derivative.

11. Dental material according to claim 1, further comprising organic and/or inorganic filler.

12. Dental material according to claim 11, wherein said dental material further contains from 10 to 90 wt. % filler.

13. Dental material according to claim 1, wherein said dental material comprises:

(a) >10 to 99.98 wt % polymerizable monomer;

(b) 0.01 to 2 wt. % thermochromic dye;

(c) 0.01 to 5 wt. % polymerization initiator;

(d) 0 to <89.98 wt. % filler; and (e) optionally 0.01 to 5 wt. % further additives.

14. Dental material according to claim 13, wherein said dental material comprises:

(a) >20 to 90 wt. % polymerizable monomer;

(b) 0.1 to 0.5 wt. % thermochromic dye;

(c) 0.01 to 5 wt. % polymerization initiator; and (d) 10 to 80 wt. % filler.

15. Dental material according to claim 14, wherein said dental material comprises 20 to 70 wt. % filler.

* * * * *